United States Patent
Payne et al.

(10) Patent No.: US 7,979,126 B2
(45) Date of Patent: Jul. 12, 2011

(54) ORIENTATION-INDEPENDENT IMPLANTABLE PULSE GENERATOR

(75) Inventors: David H. Payne, Llano, CA (US); Matthew I. Haller, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 360 days.

(21) Appl. No.: 11/550,733

(22) Filed: Oct. 18, 2006

(65) Prior Publication Data

US 2008/0097554 A1   Apr. 24, 2008

(51) Int. Cl.
*A61N 1/375* (2006.01)
(52) U.S. Cl. ........................................................ 607/36
(58) Field of Classification Search .................... 607/36, 607/33, 61
See application file for complete search history.

(56) References Cited

U.S. PATENT DOCUMENTS

| | | | |
|---|---|---|---|
| 6,067,474 A * | 5/2000 | Schulman et al. | 607/57 |
| 6,178,353 B1 | 1/2001 | Griffith et al. | |
| 6,272,382 B1 | 8/2001 | Faltys et al. | 607/57 |
| 6,411,854 B1 | 6/2002 | Tziviskos | 607/57 |
| 6,516,227 B1 | 2/2003 | Meadows | 607/46 |
| 6,553,263 B1 | 4/2003 | Meadows et al. | 607/61 |
| 6,909,917 B2 | 6/2005 | Woods et al. | 607/46 |
| 6,941,171 B2 | 9/2005 | Mann et al. | 607/39 |
| 2003/0171792 A1 | 9/2003 | Zarinetchi et al. | |
| 2004/0230250 A1 * | 11/2004 | Neumann et al. | 607/36 |
| 2005/0277999 A1 | 12/2005 | Strother et al. | |
| 2006/0129205 A1 | 6/2006 | Boveja et al. | |
| 2007/0060980 A1 * | 3/2007 | Strother et al. | 607/61 |

FOREIGN PATENT DOCUMENTS

| | | |
|---|---|---|
| EP | 1702648 A2 | 9/2006 |
| WO | 9906108 A1 | 2/1999 |

OTHER PUBLICATIONS

U.S. Appl. No. 11/305,898, filed Dec. 14, 2005, Shi et al.
Written Opinion issued in corresponding PCT application serial No. PCT/US2007/072189, issued Apr. 30, 2009.
Examiner's First Report regarding corresponding Australian patent application No. 2007313116, dated Mar. 17, 2010.

* cited by examiner

*Primary Examiner* — Scott M Getzow
*Assistant Examiner* — Amanda Patton
(74) *Attorney, Agent, or Firm* — Wong, Cabello, Lutsch, Rutherford & Brucculeri, LLP

(57) ABSTRACT

An improved structure for an implantable medical device, such as an implantable pulse generator, is disclosed. The improved device includes a charging coil for wirelessly receiving energy via induction from an external charger. The charging coil in the device is located substantially equidistantly from the two planar sides of the device case. Because the coil is substantially equidistant within the thickness of the case of the device, the device's orientation within the patient is irrelevant, at least from the standpoint of the efficiency of charging the device using the external charger. Accordingly, charging is not adversely affected if the device is implanted in the patient with the wrong orientation, or if the device flips within the patient after implantation. Moreover, because the central portion of the device naturally corresponds to the largest lateral extent within the case due to the case's curved edges, the charging coil can be made larger in area, which improves its gain vis-à-vis the external charger.

37 Claims, 5 Drawing Sheets

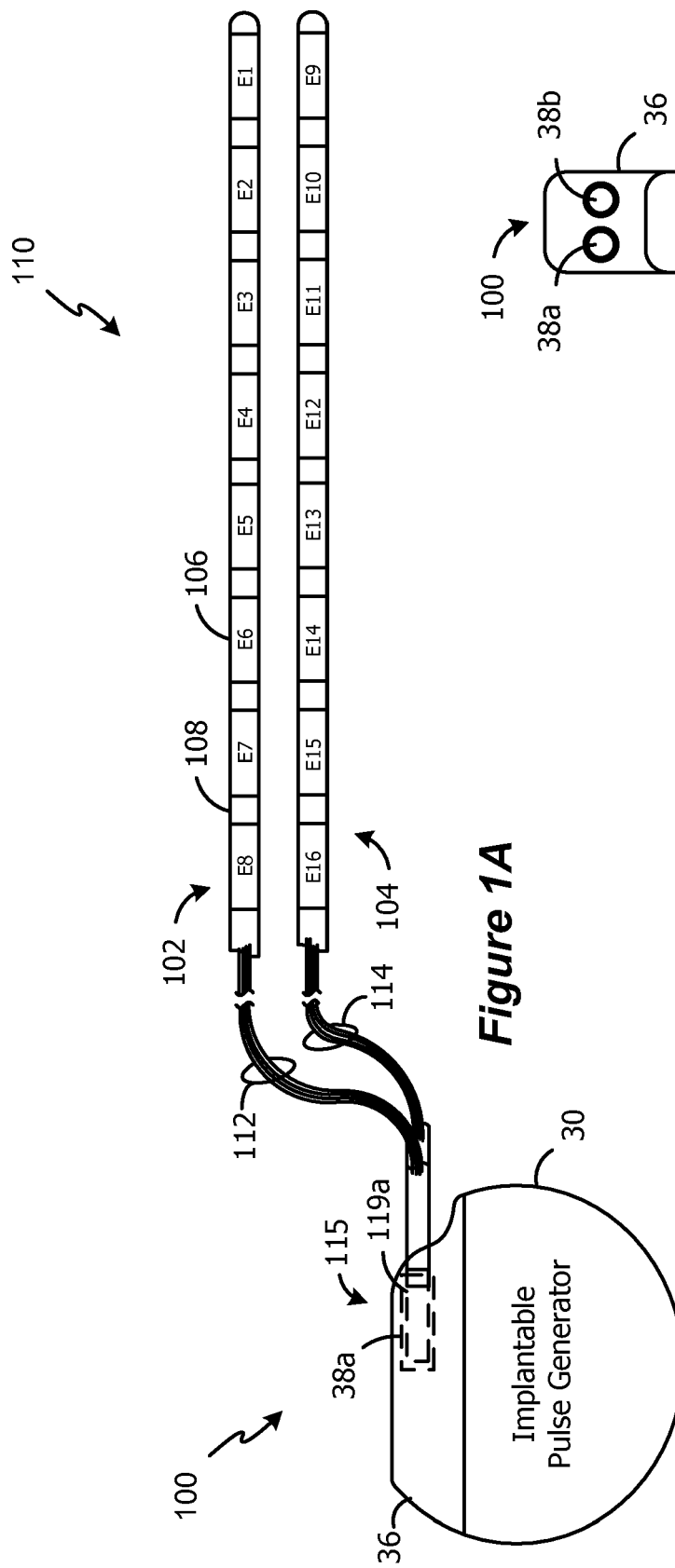
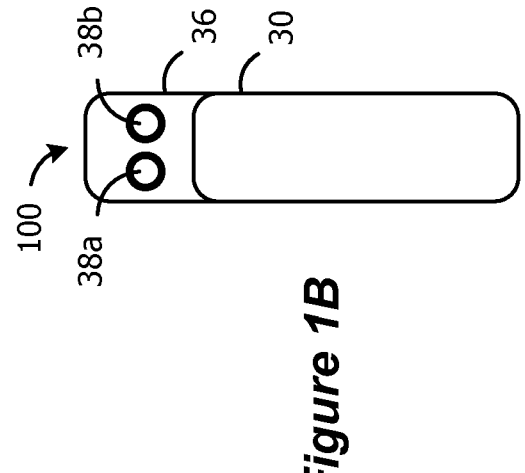
Figure 1A
Figure 1B

ORIENTATION-INDEPENDENT IMPLANTABLE PULSE GENERATOR

FIELD OF THE INVENTION

The present invention relates generally to implantable devices, and more particularly, to a fully implantable device or system for stimulating living tissue of a patient, e.g., a pulse generator used in a Spinal Cord Stimulation (SCS) system or other type of neural stimulation system.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sub-laxation, etc. The present invention may find applicability in all such applications, although the description that follows will generally focus on the use of the invention within a Spinal Cord Stimulation (SCS) system, such as that disclosed in U.S. Pat. No. 6,516,227 ("the '227 patent"), issued Feb. 4, 2003 in the name of Paul Meadows et al., which is incorporated herein by reference in its entirety.

Spinal cord stimulation is a well-accepted clinical method for reducing pain in certain populations of patients. As shown in FIGS. 1A and 1B, a SCS system typically includes an Implantable Pulse Generator (IPG) 100, which includes a biocompatible case 30 formed of titanium for example. The case 30 holds the circuitry and power source or battery necessary for the IPG to function. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112, 114, coupled to each electrode. The signal wires 112 and 114 are connected to the IPG 100 by way of an interface 115, which may be any suitable device that allows the leads 102 and 104 (or a lead extension, not shown) to be removably connected to the IPG 100. Interface 115 may comprise, for example, an electromechanical connector arrangement including lead connectors 38a and 38b configured to mate with corresponding connectors 119a and 119b on the leads 102 and 104. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary.

The electrode array 110 is typically implanted along the dura of the spinal cord, and the IPG 100 generates electrical pulses that are delivered through the electrodes 106 to the nerve fibers within the spinal column. The IPG 100 itself is then typically implanted somewhat distantly in the buttocks of the patient.

Further details concerning the structure and function of typical IPGs and IPG systems are disclosed in U.S. patent application Ser. No. 11/305,898, filed Dec. 14, 2005, which is filed herewith via an information disclosure statement and which is incorporated herein by reference.

IPGs are active devices requiring energy for operation, such as is typically provided by a battery. It is often desirable or necessary to recharge the battery within an IPG via an external charger, so that a surgical procedure to replace a power-depleted implantable pulse generator can be avoided. To wirelessly convey energy between the external charger 12 and the IPG 100, and as shown in FIG. 2A, the charger 12 typically includes an energized alternating current (AC) coil 17 that supplies energy 29 to a similar charging coil 18 located in or on the IPG 100 via inductive coupling. In this regard, the coil 17 within the external charger 12 is wrapped so as to lie substantially parallel to the plane of the coil 18 within the implantable medical device during charging. As shown, and as is well known, such a means of energy 29 transfer can occur transcutaneously, i.e., through the patients tissue 25. The energy 29 received by the IPG's coil 18 can then be stored in a rechargeable battery 26 within the IPG 100, which can then be used to power the electronic circuitry that runs the IPG 100. Alternatively, the energy 29 received can be used to directly power the IPG's electronic circuitry, which may lack a battery altogether.

As shown in FIGS. 2A and 2B, an IPG 100 typically includes an electronic substrate assembly 14 including a printed circuit board (PCB) 16, along with various electronic components 20, such as microprocessors, integrated circuits, and capacitors, mounted to the PCB 16, as well as the coil 18. Ultimately, the electronic circuitry performs a therapeutic function, such as neurostimulation. The IPG 100 further includes a plastic insert 23 with a retainer 22 for holding the electronic substrate assembly 14 in place. A feedthrough assembly 24 routes the various electrode signals from the electronic substrate assembly 14 to the lead connectors 38a, 38b, which are in turn coupled to the leads 102 and 104 (see FIGS. 1A and 1B). The IPG 100 further comprises a header connector 36, which among other things houses the lead connectors 38a, 38b. The IPG 100 can further include a telemetry antenna or coil (not shown) for receipt and transmission of data to an external device such as a hand-held or clinician programmer (not shown), which can be mounted within the header connector 36. As noted earlier, the IPG 100 usually also includes a power source, and in particular a rechargeable battery 26, which may be mounted in place by other retainers formed as a portion of the plastic insert 23.

As also noted earlier, the IPG 100 also includes a case 30, which serves to house all of the aforementioned components in a suitable manner. In particular, the case 30 comprises two case halves 32, 34 that mate with each other in a clam-shell arrangement to hermetically seal the IPG 100. The case 30 has a top surface 40, a bottom surface 42, and an edge 44 between the top and bottom surfaces 40, 42.

As can be seen from FIG. 2A, the charging coil 18 according to conventional wisdom is situated adjacent the top surface 40 of the case 30 to minimize the attenuation of the energy 29 before it is received by the charging coil 18. That is, assuming that the IPG 100 is implanted within the patient such that the bottom surface 42 faces away from the external charger 12 and the top surface 40 faces towards the external charger 12, the distance D that the energy 29 must travel before it impinges on the charging coil 18 will be minimized, which in turn maximizes the efficiency of the power transmission between the two coils 17 and 18. In addition, such top-sided placement of coil 18 requires the energy 29 only to traverse the case 30, and no other components, before it reaches the charging coil 18, which again minimizes energy 29 attenuation. While according to this conventional wisdom it is preferred to place the coil 18 as near the top surface 40 as possible, in reality it can be expected that the center of the coil is within the top 25% of the thickness T of the case (i.e., $\Delta$T <25% of T).

However, while such top-sided placement of the coil 18 within the IPG 100 has been preferred to minimize the distance D, and hence to minimize energy 29 attenuation, such a design is met with other problems.

First, because the charging coil 18 is located closely adjacent the wall of the case 30, the case 30 may electrically interact with the charging coil 18, thereby degrading the performance of the coil 18.

Second, the edge 44 of the case 30 has a curved surface 46, resulting from manufacturing limitations as well as the clinical desire to avoid sharp edges that may otherwise irritate or damage the tissue 25 surrounding the IPG 100. (The header connector 36 likewise has curved surfaces to avoid sharp edges). To locate the charging coil 18 adjacent the top surface 40 of the case 30, the charging coil 18 must necessarily be placed at the curved surface 46 of the edge 44. Unfortunately, this limits the lateral size of the coil 18, and as best shown in FIG. 2B, works a loss of lateral distance ΔL within the IPG case 30. This loss of lateral distance means that each turn of the coil encompasses a smaller area, which in turn limits the gain of the coil 18. Therefore, while placing the coil toward the top surface 40 of the case increases the gain from the perspective of minimizing the distance D from the external charger 12, it reduces the gain from the perspective of coil 18 area.

Third, when implanting the IPG 100, the physician must ensure that the top surface 40 of the case 30 faces towards the external charger 12. If the physician accidentally flips the IPG 100 during implantation such that it is in an improper top-down configuration, the external charger 12 will not be able to as effectively communicate with the IPG, since the coil 18 will be facing in the opposite direction away from external charger 12. (It has been suggested that the incidence of flipped IPG during implantation due to physician inadvertence may be on the order of 3 to 5%). Moreover, in some cases, the IPG 100 may be properly oriented when initially implanted, but then inadvertently flipped within the patient's tissue 25, such as by the patient "fiddling" with the IPG through his or her skin. Regardless of the reason, if the IPG 100 is inadvertently disoriented in the patient with in an improper top-down configuration, the power transfer efficiency benefits realized from placement of the coil 18 toward the top surface 40 of the IPG 100 are lost.

FIG. 3 illustrates another example of an IPG 50 capable of wirelessly receiving energy from an external charger 12 via inductive coupling. The IPG 50 is similar to the previously described IPG 100, with the exception that the charging coil 52 resides on the top surface of the case 54. To so mount the charging coil 52, the case 54 is encapsulated with a suitable biocompatible material 56 (e.g., epoxy), which holds the charging coil 52 in place. Thus, it can be appreciated that the charging coil 52 can be located even closer to the external charger 12, and the attenuation effect of the case 54 can be eliminated, thereby making energy 29 transfer between the external charger 12 and pulse generator 50 more efficient. Moreover, in this embodiment, because the coil 52 is on the outside of the case 54, its location is more readily apparent, making it less likely that an implanting physician would inadvertently implant in an improper top-down configuration.

There are, however, drawbacks to the design of FIG. 3. In particular, placement of the charging coil 52 on the exterior surface of the case 54 and the addition of the encapsulating material 56 increases the overall thickness of the pulse generator 50, thereby making the implanted pulse generator 50 more noticeable to the patient. Also, additional feedthrough holes must be made through the case 54 to connect the charging coil 52 to the electronic circuitry contained within the case 54, thereby increasing the design complexity and cost of the pulse generator 50.

SUMMARY

An improved structure for an implantable medical device, such as an implantable pulse generator, is disclosed. The improved device includes a charging coil for wirelessly receiving energy via induction from an external charger. The charging coil in the device is located substantially equidistantly from the two planar sides of the device case. Because the coil is substantially equidistant within the thickness of the case of the device, the device's orientation within the patient is irrelevant, at least from the standpoint of the efficiency of charging the device using the external charger. Accordingly, charging is not adversely affected if the device is implanted in the patient with the wrong orientation, or if the device flips within the patient after implantation. Moreover, because the central portion of the device naturally corresponds to the largest lateral extent within the case due to the case's curved edges, the charging coil can be made larger in area, which improves its gain vis-a-vis the external charger.

BRIEF DESCRIPTION OF THE DRAWINGS

The above and other aspects of the present invention will be more apparent from the following more particular description thereof, presented in conjunction with the following drawings wherein:

FIGS. 1A and 1B show an implantable pulse generator (IPG), and the manner in which an electrode array is coupled to the IPG in accordance with the prior art.

Corresponding reference characters indicate corresponding components throughout the several views of the drawings.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims and their equivalents.

At the outset, it is noted that the present invention may be used with an implantable pulse generator (IPG), or similar electrical stimulator and/or electrical sensor, that may be used as a component of numerous different types of stimulation systems. The description that follows relates to use of the invention within a spinal cord stimulation (SCS) system. However, it is to be understood that the invention is not so limited. Rather, the invention may be used with any type of implantable electrical circuitry that could benefit from an improved structure for positioning of the charging coil. For example, the present invention may be used as part of a pacemaker, a defibrillator, a cochlear stimulator, a retinal stimulator, a stimulator configured to produce coordinated limb movement, a cortical and deep brain stimulator, or in any other neural stimulator configured to treat urinary incontinence, sleep apnea, shoulder sublaxation, etc.

The improved structure and arrangement of an IPG 190 will now be described in further detail with reference to FIG. 4, 5A and 5B, which respectively show the improved structure in exploded perspective, top-down, and cross-sectional views. To the extent structures in the improved IPG 190 are similar in function to those discussed earlier in the Background section, such functionality is not repeated again here.

Figure 2A:
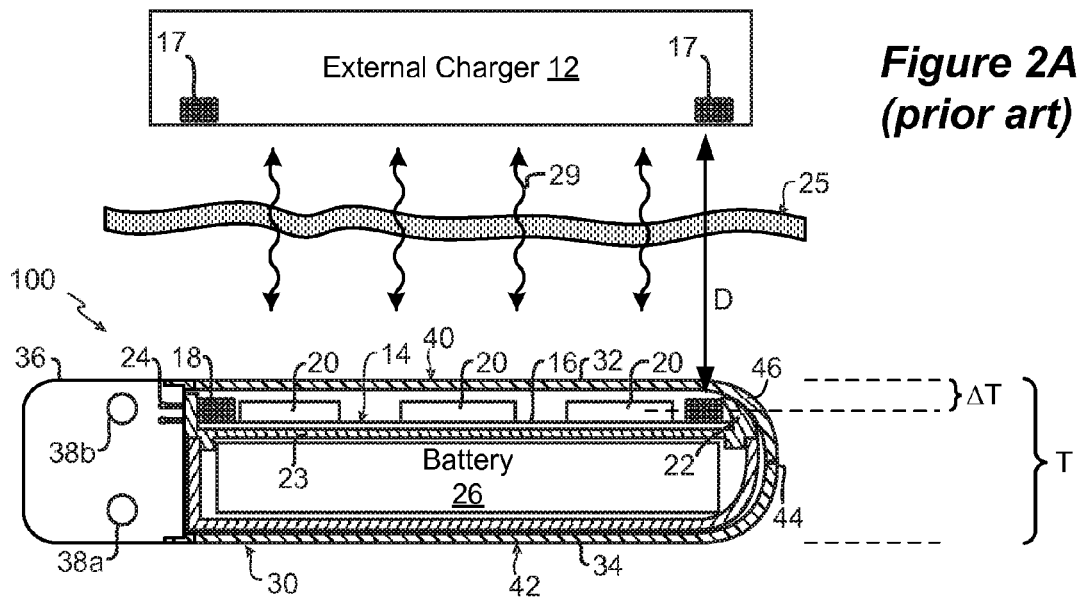
FIGS. 2A and 2B respectively show cross-sectional and top-down views of a prior art implantable pulse generator, particularly showing one way of configuring a charger coil within the interior of a case for the IPG.
Figure 2B:
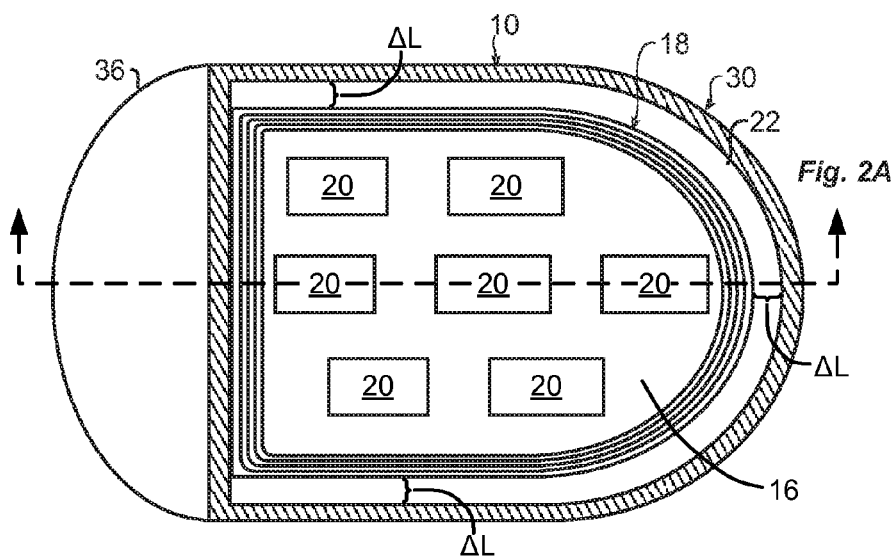
Figure 3:
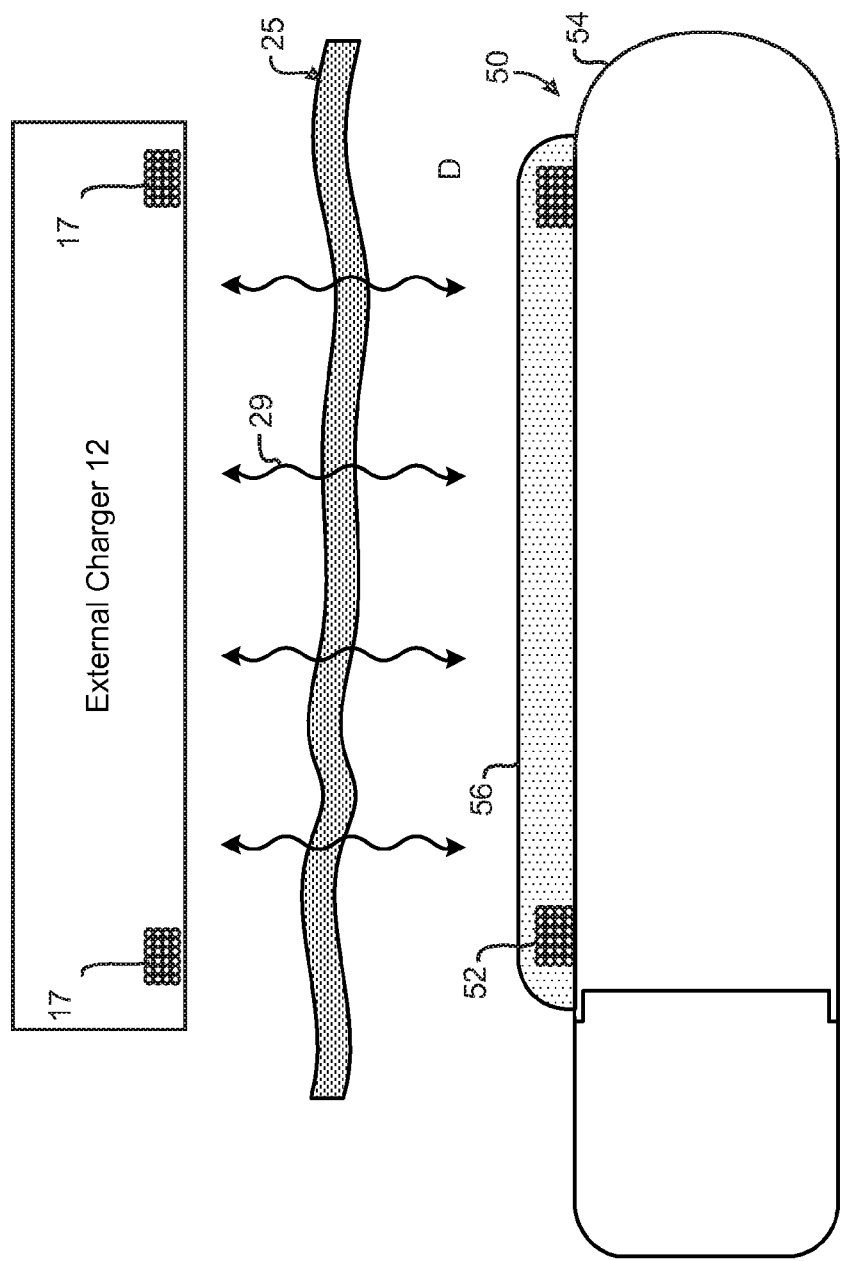
FIG. 3 shows a side view of another prior art implantable generator, particularly showing another way of configuring a charger coil exterior to the case of the IPG.

The IPG 190 generally comprises a case 200 comprising a header connector 202, an electronic substrate assembly 204, a feedthrough assembly 223 for coupling the electronic substrate assembly 204 with the header connector 202 and ultimately with the lead connectors 205a, 205b, and an AC charging coil 208. The electronic substrate assembly 204 includes a printed circuit board (PCB) 210 on which various electronic components 212 are mounted or otherwise carried. The electronic components 212 can be, e.g., the electronic components described above with respect to FIGS. 2A and 2B. The charging coil 208 may be any suitable coil capable of creating a current in response to magnetic energy, but in the illustrated embodiment, takes the form of double-layer copper coil. Although not strictly required in all embodiments of the invention, the IPG 190 also preferably includes a power source 206, such as a rechargeable battery.

The IPG 190 preferably includes a unitary plastic insert 250 having the various retaining mechanism to hold the various components of the IPG 190 in place. Such an insert 250 in a preferred embodiment resides only in the bottom half 220 of the case, but this is not strictly necessary. In the embodiment shown, the insert 250 comprises first retainers 214 for supporting the coil 208 within the case 200, and second retainers 216 for supporting the power source 206 within the case 200. The battery 206 and charging coil 208 serve to provide a means for continuously supplying the IPG 190 with renewable energy, such as was described earlier with respect to power source 26 and coil 18 (see FIG. 2A). As compared to the prior art, the battery 206 is located at the above the PCB 210, and on the same side of the PCB 210 as the electronic components 212.

In the illustrated embodiment, the case 200 is a single hermetically-sealed rounded case having, for instance, a diameter X (FIG. 5A) of less than 55 mm and a maximum thickness T (FIG. 5B) of 10 mm. Preferably, the thickness of the case 200 is 7 mm or less to make the IPG 190, when implanted under the skin, more inconspicuous to the user. In any event, the exact dimensions of the case 200 are not critical to the invention and can vary in size, and would be expected to shrink as technology progresses. In the illustrated embodiment, the case 200 has two case halves 218, 220 that mate together in a clam-shell arrangement to house the components. Alternatively, the case 200 may have a unibody construction that includes a closed end and an open end through which the various components are loaded during assembly.

Figure 4:
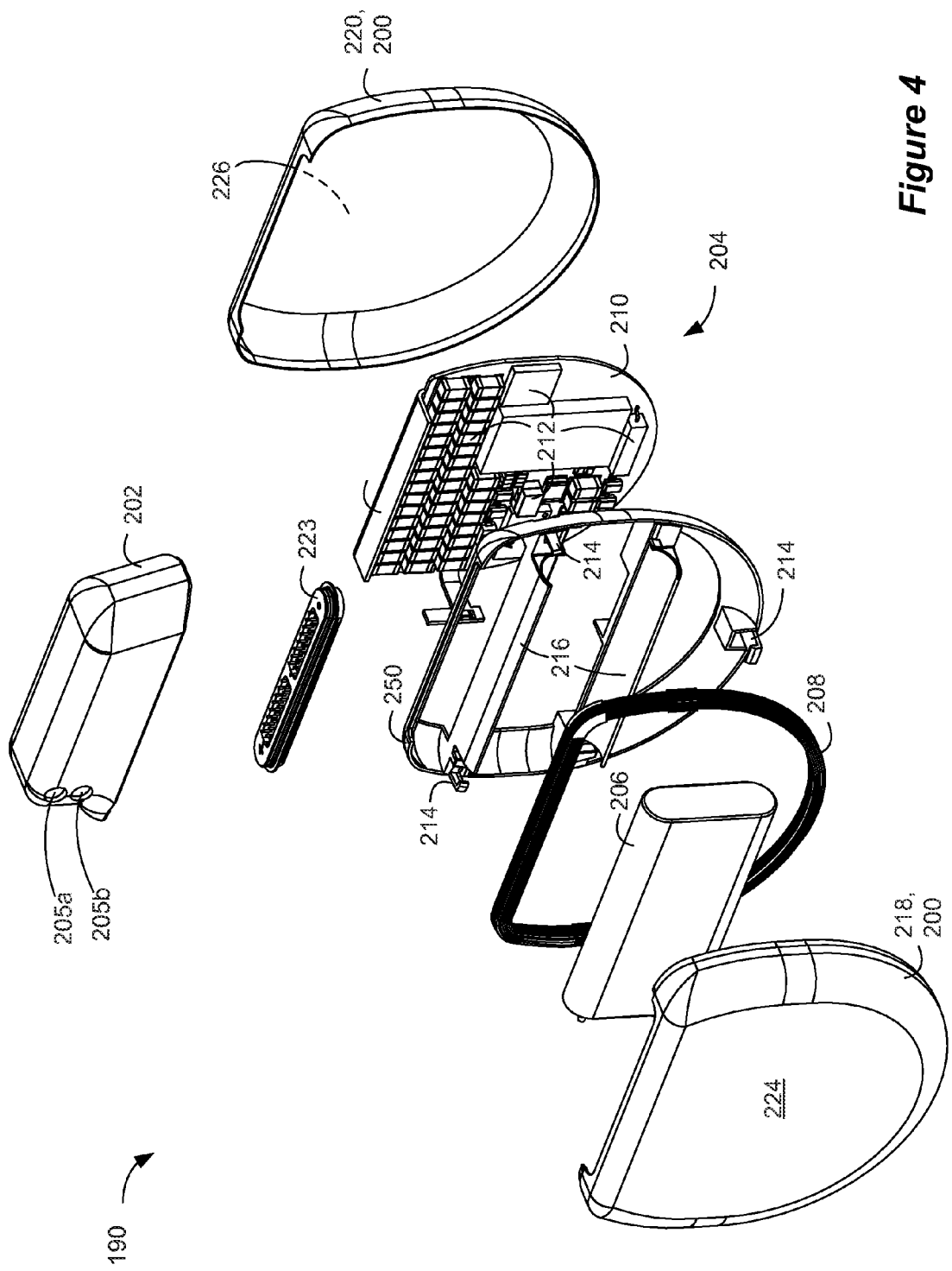
FIG. 4 shows an exploded perspective view of an improved IPG structure in accordance with the prior art in which the charging coil is substantially equidistant within the thickness of the IPG case.
Figure 5A:
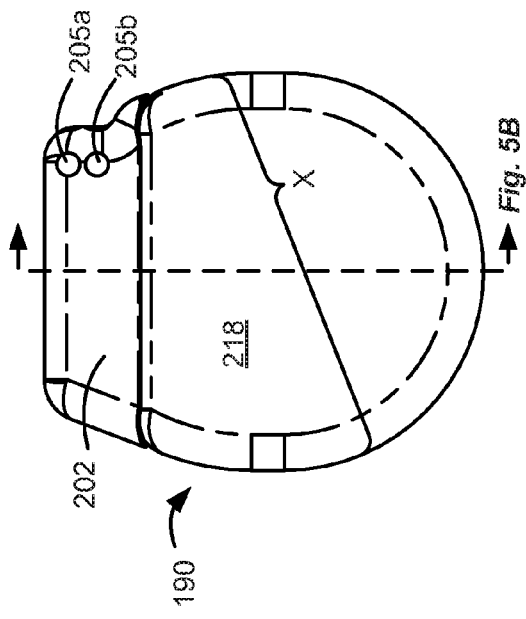
FIGS. 5A and 5B respectively show top-down and cross-sectional views of the improved IPG structure of FIG. 4.
Figure 5B:
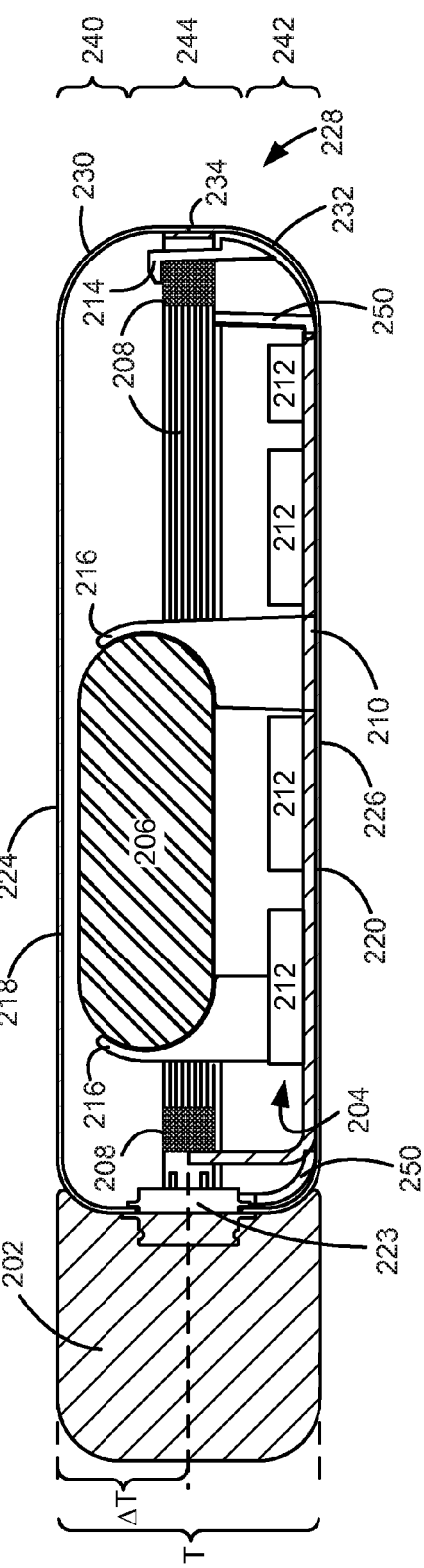

The case 200 is preferably composed of a biologically compatible material having a relatively high resistivity to reduce heat generated by eddy currents induced in the case 200 during recharging of the IPG 190 via the external charger 12 (not shown in FIGS. 4, 5A and 5B). The wall thickness of the case 200 is also minimized as much as structurally possible to further increase the resistance in the case 200. Titanium 6-4 (6% aluminum, 4% vanadium), which has a resistivity of 177 micro-ohms centimeter (60 times the resistivity of copper), is a suitable material from which the case 200 can be manufactured. Alternatively, the case 200 may be fabricated from another metal, such as Titanium 8-1-1 (8% aluminum, 1% molybdenum, 1% vanadium), Titanium 3-2.5 (3% aluminum, 2.5% vanadium), Haynes® 25, or from a ceramic material, such as alumina ($Al_2O_3$) or zirconia ($ZrO_2$). If the case 200 is fabricated from a ceramic material, the case 200 can be filled with a potting material, such as that described in U.S. Pat. No. 6,411,854, which is incorporated herein by reference.

The header connector 202 is mounted to the case 200 using suitable means, such as welding. As briefly mentioned earlier, the header connector 202 includes a feedthrough assembly 223 which mates with corresponding pins extending from the electronic substrate assembly 204. A data telemetry coil (not shown) may also be located in the header connector 202 and coupled to the input of the electronic substrate assembly 204 via the feedthrough assembly 223 or by other means.

In the illustrated embodiment, the case 200 has a standard shape. As best shown in FIG. 5B, the case 200 has substantially flat, external, opposing surfaces 224 and 226 respectively on the top and bottom case halves 218 and 220, with an edge 228 located between them. The edge 228 preferably has upper and lower curved surfaces 230 and 232 in the top and bottom case halves 218 and 220 so that the case 200 does not have any sharp edges. (The header connector 202 likewise lacks sharp edges). The edge 228 further has a flat surface 234 between the curved surfaces 230 and 232. Alternatively, the edge 228 can comprise a single continuous curved surface without an intervening flat surface 234. In any event, these various curved surfaces define various case regions, i.e., an upper region 240 corresponding to upper curved surface 230, a lower region 242 corresponding to lower curved surface 232, and a center region 244 corresponding to the flat surface (or center "point" if no flat surface 234 is present).

In accordance with embodiments of the invention, and as shown in FIG. 5B, the charging coil 208 in the improved IPG 190 is wound in a plane within or at the center region 244 (or center point as the case may be). This means the charging coil 208 is preferably mounted such that its plane lies substantially parallel to, and substantially equidistant between, the opposing surfaces 224 and 226 of the case 200. In other words, the center of the coil 208 is located at the center point of the thickness T of the case (i.e., $\Delta T \approx 50\%$ of T), which defines a maximum lateral area within the case. This serves many useful purposes when compared to the prior art designs of FIGS. 1A through 3.

First, because the charging coil 208 is not located closely adjacent the wall of the case 200, the case 200 is less prone to electrically interacting with the coil 208, thereby improving its performance.

Second, because of the curved surfaces 230 and 232, the center region 244 has a greater lateral extent than either of the upper or lower regions 240 or 242. This allows each turn of the charging coil 208 to encompass a larger area, which increases the gain of the coil 208, which in turn improves efficiency of energy transfer between the external charger 12 and the IPG 190. In other words, and in comparison to the prior art illustration of FIG. 2B, the loss of lateral distance within the IPG case 200 ($\Delta L$) is reduced or eliminated. From a charging perspective, the increased size of the charging coil 208 compensates for the increased distance between it and the top surface 224 of the case 200.

Third, and perhaps most significantly, when the charging coil 208 is mounted at the center region 244 of the case 200, the efficient of energy transfer from the external charger 12 to the coil 208 is made essentially independent of the orientation of the IPG 190 when implanted in a patient. In other words, it is basically irrelevant (at least from a charging standpoint) whether the IPG 190 is oriented within the patient with its top surface 224 toward the external charger 12, or with its bottom surface 226 toward the charger. Because the coil 208 is located substantially equidistantly within the case 200, the charger-to-IPG distance D (see FIG. 2A) is the same, meaning that the amount of charging energy received is substantially equivalent for either orientation. In other words, the magnitude of the energy received by the coil 208 is substantially the same regardless of which of the surfaces 224 or 226 the energy traverses. Thus, a physician need not be concerned with whether the IPG 190 is facing up or facing down when implanting it within a patient, and it is of little concern (to charging efficiency at least) should the IPG 190 flip inside the patient after implantation.

While the charging coil 208 has been described as useful in charging a rechargeable power source, such as a rechargeable battery 206, it should be recognized that use of a rechargeable battery or other power source (e.g., a capacitor) is not strictly necessary. For example, the charging coil 208 can be used to provide power directly to the electronic components within the IPG 190. In such a case, the IPG 190 may or may not have an on-board power source, whether or not rechargeable. Of course, if no power source is present, the energy 29 transmitted by the external charger 12 may need to be continuous, or at least periodic.

Of course, one skilled in the art will recognize that embodiments of the invention will still have utility even if the charging coil 208 is not positioned exactly at the center of the case (i.e., $\Delta T \approx 50\%$ of T), and even if the energy transfer from the external charger 12 to the coil 208 is not exactly equivalent from both sides of the IPG. In this regard, the a coil "substantially equidistant within the thickness of the case" or "substantially equidistant between opposing surfaces of the case" should be understood as encompassing a plus or minus 10% deviation from the center of the case (i.e., 40% of $T \leq \Delta T \leq 60\%$ of T).

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device, comprising:
   a case having opposing external surfaces;
   electronic circuitry contained within the case for performing a therapeutic function for the patient; and
   a coil contained within the case configured for wirelessly receiving energy from an external device, wherein the received energy provides power to the electronic circuitry, the coil being wound in a plane parallel to the surfaces, wherein the coil is substantially equidistant between the surfaces,
   wherein the case in cross section though the external surfaces has edges comprised of curved regions each meeting with only one of the external surfaces and a straight center region between the curved regions, and wherein the coil in the cross section is positioned entirely within the straight center regions of the edges.

2. The device of claim 1, where the therapeutic function is neurostimulation.

3. The device of claim 1, further comprising at least one electrode coupled to the electronic circuitry for implementing the therapeutic function.

4. The device of claim 1, wherein the received energy provides power to recharge a battery within the case that provides the power to the electronic circuitry.

5. The device of claim 1, wherein the electronic circuitry is carried by a printed circuit board.

6. The device of claim 5, wherein the electronic circuitry comprises a battery and components, and wherein the battery is positioned above the components.

7. The device of claim 6, wherein the electronic circuitry comprises a battery and components, and wherein the battery is positioned on the same side of the printed circuit board as the components.

8. The device of claim 1, wherein the straight center regions of the edges defines a maximum lateral area for the coil within the case, and wherein the coil in the cross section is positioned to encompass the maximum lateral area.

9. An implantable medical device, comprising:
   a case having opposing external surfaces;
   electronic circuitry contained within the case for performing a therapeutic function for the patient;
   a battery for powering the electronic circuitry; and
   a coil contained within the case configured for wirelessly receiving energy from an external device, wherein the received energy provides power to recharge the battery, the coil being wound in a plane parallel to the surfaces,
   wherein the case in cross section though the external surfaces has aft edges comprised of curved regions each meeting with only one of the external surfaces and a straight center region between the curved regions, and wherein the coil in the cross section is positioned entirely within the straight center regions of the edges.

10. The device of claim 9, where the therapeutic function is neurostimulation.

11. The device of claim 9, further comprising at least one electrode coupled to the electronic circuitry for implementing the therapeutic function.

12. The device of claim 9, wherein the electronic circuitry is carried by a printed circuit board.

13. The device of claim 12, wherein the electronic circuitry comprises components, and wherein the battery is positioned above the components.

14. The device of claim 12, wherein the electronic circuitry comprises components, and wherein the battery is positioned on the same side of the printed circuit board as the components.

15. An implantable stimulator device, comprising:
   a case having opposing external surfaces;
   at least one electrode for providing therapeutic stimulation to a patient;
   electronic circuitry contained within the case for providing the therapeutic stimulation to the at least one electrode;
   a battery for powering the electronic circuitry; and
   a coil contained within the case configured for wirelessly receiving energy from an external device, wherein the received energy provides power to recharge the battery,
   wherein the case in cross section though the external surfaces has edges comprised of curved regions each meeting with only one of the external surfaces and a straight center region between the curved regions, and wherein the coil in the cross section is positioned entirely within the straight center regions of the edges.

16. The device of claim 15, further comprising a header connector coupled to the case for coupling the at least one electrode to the electronic circuitry.

17. The device of claim 15, wherein the electronic circuitry is carried by a printed circuit board.

18. The device of claim 17, wherein the electronic circuitry comprises components, and wherein the battery is positioned above the components.

19. The device of claim 17, wherein the electronic circuitry comprises components, and wherein the battery is positioned on the same side of the printed circuit board as the components.

20. A system, comprising:
    an implantable medical device, comprising:
        a case having opposing external surfaces;
        electronic circuitry contained within the case for performing a therapeutic function for the patient; and
        a coil contained within the case configured for wirelessly receiving energy, wherein the received energy provides power to the electronic circuitry, the coil being wound in a plane parallel to the surfaces, wherein the coil is substantially equidistant between the surfaces,
    wherein the case in cross section though the external surfaces has edges comprised of curved regions each meeting with only one of the external surfaces and a straight center region between the curved regions, and wherein the coil in the cross section is positioned entirely within the straight center regions of the edges; and
    an external charger for producing the energy.

21. The system of claim 20, where the therapeutic function is neurostimulation.

22. The system of claim 20, wherein the implantable medical device further comprises at least one electrode coupled to the electronic circuitry for implementing the therapeutic function.

23. The system of claim 20, wherein the received energy provides power to recharge a battery within the case that provides the power to the electronic circuitry.

24. The system of claim 20, wherein the external charger produces the energy via energizing a coil within the external charger.

25. The system of claim 24, wherein the coil within the external charger is wrapped so as to lie substantially parallel to the plane of the coil within the implantable medical device during charging.

26. The system of claim 20, wherein the electronic circuitry is carried by a printed circuit board within the implantable medical device.

27. The system of claim 26, wherein the electronic circuitry comprises a battery and components, and wherein the battery is positioned above the components.

28. The system of claim 26, wherein the electronic circuitry comprises a battery and components, and wherein the battery is positioned on the same side of the printed circuit board as the components.

29. The system of claim 20, wherein the straight center regions of the edges defines a maximum lateral area for the coil within the case, and wherein the coil in the cross section is positioned to encompass the maximum lateral area.

30. A system, comprising:
    an implantable medical device, comprising:
        a case having opposing external surfaces;
        electronic circuitry contained within the case for performing a therapeutic function for the patient;
        a battery for powering the electronic circuitry; and
        a coil contained within the case configured for wirelessly receiving energy from an external device, wherein the received energy provides power to recharge the battery, the coil being wound in a plane parallel to the surfaces,
    wherein the case in cross section though the external surfaces has edges comprised of curved regions each meeting with only one of the external surfaces and a straight center region between the curved regions, and wherein the coil in the cross section is positioned entirely within the straight center regions of the edges; and
    an external charger for producing the energy.

31. The system of claim 30, where the therapeutic function is neurostimulation.

32. The system of claim 30, wherein the implantable medical device further comprises at least one electrode coupled to the electronic circuitry for implementing the therapeutic function.

33. The system of claim 30, wherein the external charger produces the energy via energizing a coil within the external charger.

34. The system of claim 33, wherein the coil within the external charger is wrapped so as to lie substantially parallel to the plane of the coil within the implantable medical device during charging.

35. The system of claim 30, wherein the electronic circuitry is carried by a printed circuit board within the implantable medical device.

36. The system of claim 35, wherein the electronic circuitry comprises components, and wherein the battery is positioned above the components.

37. The system of claim 35, wherein the electronic circuitry comprises components, and wherein the battery is positioned on the same side of the printed circuit board as the components.

* * * * *